(12) United States Patent
Takemoto et al.

(10) Patent No.: US 9,242,932 B2
(45) Date of Patent: Jan. 26, 2016

(54) MESO-BILIVERDIN COMPOSITIONS AND METHODS

(71) Applicant: Utah State University, North Logan, UT (US)

(72) Inventors: Jon Y. Takemoto, North Logan, UT (US); Dong Chen, Logan, UT (US); Cheng-Wei T. Chang, Logan, UT (US)

(73) Assignee: Utah State University, North Logan, UT (US)

( * ) Notice: Subject to any disclaimer, the term of this patent is extended or adjusted under 35 U.S.C. 154(b) by 222 days.

(21) Appl. No.: 13/650,842

(22) Filed: Oct. 12, 2012

(65) Prior Publication Data

US 2013/0096318 A1    Apr. 18, 2013

Related U.S. Application Data

(60) Provisional application No. 61/546,442, filed on Oct. 12, 2011.

(51) Int. Cl.
*C07D 207/38* (2006.01)
*C07D 207/44* (2006.01)
*C12P 17/16* (2006.01)

(52) U.S. Cl.
CPC ............ *C07D 207/38* (2013.01); *C07D 207/44* (2013.01); *C12P 17/165* (2013.01)

(58) Field of Classification Search
None
See application file for complete search history.

(56) References Cited

U.S. PATENT DOCUMENTS

| 2011/0104728 A1 | 5/2011 | Takemoto |
| 2011/0217764 A1 | 9/2011 | Christenson |

OTHER PUBLICATIONS

Rüdiger, et al., Euro. J. Biochem., 7:509 (1969).*
Brown, S.B., The biosynthesis of the chromophore of phycocyanin, Biochem. J.1989, vol. 261, pp. 259-263.
Rhie, Gi-Eun et al., Biosynthesis of Phycobilins, Journal of Biological Chemistry, 1992, vol. 267, No. 23, Aug. 15 issue, pp. 16088-16093.
Lemberg, R., Bile Pigments, Biochem J. vol. 28, Part 3, 1934, pp. 978-987.
International Search Report and Written Opinion for PCTUS/2012/060086, Oct. 12, 2012.
Khatib, Water to Value-Produced Water Management for Sustainable Field Development of Mature and Green Fields, Journal of Petroleum Technology, Jan. 2003, p. 26-28.
Silveira, Optimization of Phycocyanin Extraction from Spirulina Ethanol Using Factorial Design, Bioresource Technology, Sep. 8, 2006, p. 1629-1634, vol. 98, No. 8, Elsevier, Cambridge.MA.
Beuhler, Cleavage of Phycocyanobilin from C-phycocyanin Separation and Mass Apectral Indetification of the Products, Journal of Biological Chemistry, Apr. 25, 1976, p. 2405-2411, vol. 251, No. 8, American Society for Biochemistry and Molecular Biology, Rockville, MD.
Extended European Search Report, application No. 12839361.8 (mailing date Mar. 3, 2015).
Suresh et al., The detection of HG2+ by cyanobacteria in aqueous media, 2009 Chemical Communications 2496-2498 (Apr. 2, 2009).
Watson et al, Differences in the Formation of Mesobiliviolin and Glaucobilin from d- and i-Urobilins, 235:3 The Journal of Biological Chemistry 787-794 (Mar. 1, 1960).

* cited by examiner

*Primary Examiner* — Michael Barker

(57) ABSTRACT

Methods and materials for producing meso-biliverdin are provided where the methods include reacting phycocyanobilin with an amphoteric compound in a solvent to yield meso-biliverdin.

13 Claims, No Drawings

MESO-BILIVERDIN COMPOSITIONS AND METHODS

CROSS-REFERENCE TO RELATED APPLICATION

This application claims priority to U.S. Provisional Application No. 61/546,442, filed Oct. 12, 2011, the entirety of which in hereby incorporated by reference.

BACKGROUND

1. Field of the Invention

The present disclosure relates to chemical compositions and their production. More specifically, it relates to meso-biliverdin and methods of producing meso-biliverdin.

2. Description of Related Art

Biliverdin IXα is the most common form of several biliverdin isomers found in nature (shown below).

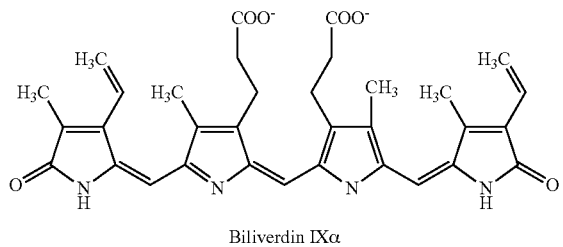

Biliverdin IXα

Biliverdin IXα is produced in animals, plants and microbes. In biological processes, biliverdin IXα is known to undergo conversion to bilirubin IXα that in turn associates with cell membranes where it quenches the propagation of reactive oxygen species. U.S. patent application Ser. No. 12/939,880, filed on Nov. 4, 2010 and incorporated herein by reference in its entirety, describes a production process for biliverdin IXα and its associated multiple uses.

Conventionally, biliverdin IXα and other biliverdin isomers are costly and difficult to produce, particularly in amounts that would be necessary for clinical studies and/or clinical applications. Thus, as exemplified in U.S. patent application Ser. No. 12/939,880, there is a need for new and improved production methods for biliverdin and associated isomers.

BRIEF SUMMARY

The present disclosure in aspects and embodiments addresses these various needs and problems by providing methods and materials for producing meso-biliverdin. The methods include reacting phycocyanobilin with an amphoteric compound in a solvent to yield meso-biliverdin. Suitable amphoteric compounds may include at least one of sodium bicarbonate, potassium carbonate, and sodium carbonate. Suitable solvents may include at least one of ethanol and tert-butanol

DETAILED DESCRIPTION

The present disclosure covers methods, compositions, reagents, and kits for the production of meso-biliverdin (shown below).

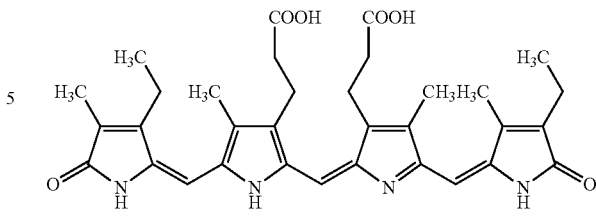

In the following description, numerous specific details are provided for a thorough understanding of specific preferred embodiments. However, those skilled in the art will recognize that embodiments can be practiced without one or more of the specific details, or with other methods, components, materials, etc. In some cases, well-known structures, materials, or operations are not shown or described in detail in order to avoid obscuring aspects of the preferred embodiments. Furthermore, the described features, structures, or characteristics may be combined in any suitable manner in a variety of alternative embodiments. Thus, the following more detailed description of the embodiments of the present invention is not intended to limit the scope of the invention, but is merely representative of the various embodiments of the invention.

In this specification and the claims that follow, singular forms such as "a," "an," and "the" include plural forms unless the content clearly dictates otherwise. All ranges disclosed herein include, unless specifically indicated, all endpoints and intermediate values. In addition, "optional" or "optionally" refer, for example, to instances in which subsequently described circumstance may or may not occur, and include instances in which the circumstance occurs and instances in which the circumstance does not occur. The terms "one or more" and "at least one" refer, for example, to instances in which one of the subsequently described circumstances occurs, and to instances in which more than one of the subsequently described circumstances occurs.

In embodiments, the methods may comprise at least one of the following steps: (1) microbial production, (2) phycocyanobilin extraction, and (3) conversion of phycocyanobilin to meso-biliverdin.

Microbial Production

Any suitable cyanobacterial species (also known as "blue green alga") or rhodophyte or cyptophyte species (also knows as red or cryptomonad alga, respectively) may be used to produce phycocyanin, a bile pigment-protein complex that efficiently harvests light for photosynthetic cyanobacteria. Phycocyanin comprises phycocyanobilin (show below) as the bile pigment chromophore, which is covalently bound (via thiol linkages) to the protein component.

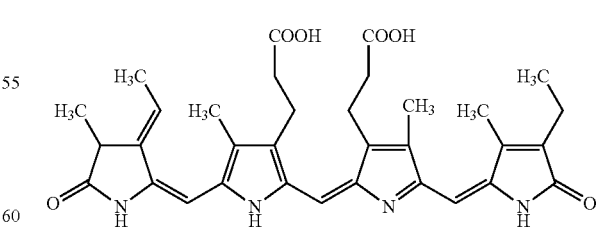

Phycocyanobilin

Some cyanobacteria or rhodophytes will produce phycocyanin in concentrations up to and including ~50% of the total cell soluble protein. Such production may occur when the cyanobacteria need to gather as much light as possible, for example, under low light conditions. As such, cyanobacteria, rhotophytes, and cytophytes with a propensity to produce higher concentrations of phycocyanin are ideally suited for the instant methods. However, any cyanobacteria, rhodophyte, or cryptophyte species or one or more species may be used. For example, *Arthrospira platensis* (also referred to as *Spirulina*) may be used.

Any suitable growth medium may also be employed to grow phycocyanin-producing species. For example, conventional growth media may be used. In addition, or as an alternative to conventional growth mediums, polluted and/or waste water may also be used exclusively or in combination with conventional growth mediums. Exemplary polluted and/or waste waters include: produced, sanitary, commercial, industrial, agricultural, and/or surface runoff waste water. Produced water also includes contaminated waste water generated from oil and natural gas recovery operations. An estimated 77 billion gallons of produced water was produced world-wide in 1999 (3 bbl per bbl of crude oil) (Katib and Verbeek, 2003). Produced water is environmentally unsuitable for discharge into surface waters. By using polluted water sources, the water is at least partially cleaned and the bioremediation of the waste water is encouraged.

In some embodiments, the waste water may be shaken or otherwise treated to eliminate volatile gases. Depending on the nutrients in the water, the water may be supplemented with suitable nutrients and growth factors, such as sodium nitrate in amounts of from about 15 to about 1500 mg per L and/or dibasic potassium phosphate in amounts of from about 2 to about 200 mg per L).

Growth conditions may include shaking, stirring, and agitating. The culture is exposed to either natural and/or artificial light for periods of two days to two or more weeks depending on nutrient concentrations and culture temperatures. Culture temperatures may be from about 20° C. to about 40° C., such as from about 25° C. to 33° C., or about 26° C.

In some applications, rotating algal bioreactors in large quantities of water may be employed to create biofilms as described in U.S. Patent Application Publication No. 2011/0217764.

Extraction of Phycocyanobilin

Any suitable extraction method for extracting phycocyanobilin from cyanobacteria may be used. Although the culture conditions described above may be employed, any source of cyanobacteria may be used in the extraction process. If the cells are in a culture medium, they must first be harvested or further concentrated. The cells may be lysed and dried or lysed and kept in a slurry, paste, or partially dried condition. In some embodiments, pre-dried cyanobacteria, rhodophytes, or cryptophytes, such as pre-dried *Spirulina*, may be used as a phycocyanobilin source rather than organisms specifically cultured for extraction.

In some embodiments, the extraction process may be separated into the following steps: (1) phycocyanin extraction, (2) cleavage of phycocyanobilin from phycocyanin, and (3) phycocyanobilin purification.

Any suitable bacterial cell breakage and fractionation method may be used for extraction and recovery of phycocyanin. For example, a slurry containing water and cyanobacterial cells may be prepared by shaking, centrifugation to sediment cells, cell breakage (mechanical or chemical), centrifugation to sediment unbroken cells and debris, and recovery of non-sedimenting cell extract, followed by the addition of ammonium sulfate ($(NH_4)_2SO_4$) to precipitate phycocyanin. After incubation and additional centrifugation, sedimented dark-blue phycocyanin may be collected and washed with a washing solvent, for example, methanol or ethanol. See, e.g., Silveira et al., Optimization of phycocyanin extraction from *Spirulina platensis* using factorial design, Bioresour Technol. 2007, 98(8):1629-34.

Cleavage of phycocyanobilin from phycocyanin may be undertaken by any suitable method. For example, phycocyanin may be boiled in a solvent, such as methanol or ethanol, under reflux conditions to cleave the bonds between the pigment and protein. See, Beuhler et al., Cleavage of phycocyanobilin from C-phycocyanin. Separation and mass spectral identification of the products, J. Biol. Chem. 1976, 251(8): 2405-2411

The phycocyanobilin may be further concentrated and purified by centrifugation, or other suitable purification method, followed by extraction of the phycocyanobilin by a suitable method, such as with chloroform. After this extraction, the chloroform solution may be added to an organic solvent, such as hexane, followed by centrifugation to yield pure phycocyanobilin powder.

Conversion of Phycocyanobilin to Meso-Biliverdin

Phycocyanobilin from any suitable source may be converted to meso-biliverdin. Suitable phycocyanobilin includes phycocyanin extracted by the above-described extraction process. Other sources of phycocyanobilin may also be used. To yield the desired meso-biliverdin, an isomerization of phycocyanobilin is carried out. In the past, isomerization and/or oxidation was carried out with potassium hydroxide (KOH), methanol (MeOH), and chloroform. See, e.g., Beuhler et al., Cleavage of phycocyanobilin from C-phycocyanin. Separation and mass spectral identification of the products, J. Biol. Chem. 1976, 251(8):2405-2411. As an alternative to using the caustic and harsh reactants, particularly KOH, an alternative method of isomerization is described below.

To isomerize phycocyanobilin to meso-biliverdin, phycocyanobilin is dissolved in a solvent along with an amphoteric compound. Suitable amphoteric compounds include, for example, sodium bicarbonate ($NaHCO_3$), potassium carbonate ($K_2CO_3$), sodium carbonate, and combinations thereof. Suitable solvents include, for example, ethanol (EtOH), such as reagent grade ethanol (95%). Similarly, tert-butyl alcohol may be used as a solvent.

The ratios of the reagents may be varied. In some embodiments, 1 to 5 folds, such as 3, 4, or 5 folds, in weight of $NaHCO_3$ and $K_2CO_3$ compared to phycocyanobilin may be used. A sufficient amount of solvent may be used to dissolve the reactants. For example, about 3 mL ethanol may be used with about 5 mg phycocyanobilin.

The reaction is permitted to run for about 12-48 hours, such as from about 24-48 hours, or about 24 hours at about 80° C. The reaction mixture may be filtered through Celite and the residue was washed and filtered with more ethanol. The solvent may removed to provide the meso-BV and may be further purified if desired by HPLC.

This isomerization reaction has numerous advantages over prior methods, such as the method mentioned above. Advantages include, for example, 1) avoiding the use of KOH, which is caustic and can be difficult to dispose of after product purification; and 2) avoiding the use of methanol and chloroform, which are toxic and can also be difficult to dispose of after purification.

In some embodiments, the entire process of (1) microbial production, (2) phycocyanobilin extraction, and (3) conversion of phycocyanobilin to meso-biliverdin may be carried out with natural compounds, such as ethanol for a reaction solvent and washing solvent.

The following examples are illustrative only and are not intended to limit the disclosure in any way.

EXAMPLES

Example 1

Cyanobacteria Production

*Arthrospira platensis* was grown on produced water that has been previously shaken for several days to eliminate volatile gases and supplemented with sodium nitrate and potassium phosphate. Growth occurred with shaking and fluorescent light over several days to two weeks at 26° C. The cells were then harvested and dried.

Example 2

Phycocyanobilin Extraction

Phycoyanin Extraction.

The extraction was carried out by adding 160 g *Spirulina* powder to 2 L (2000 mL) of purified water (0.08 g/mL) and shaking in a rotary shaker overnight (16 hours) at 200 rpm and 37° C. Sample was centrifuged 90 minutes at 9500 RPM and 4° C. 530 g $(NH_4)_2SO_4$ (MW. 132.14) was added to the supernatant to give a 50% saturated (NH4)2SO4 solution. The solution was incubated in ice water (0° C.) for 30 minutes. After centrifugation at 9500 rpm 30 minutes, the dark-blue Phycoyanin was collected and washed by 700 mL methanol. Repeat the centrifugation and washing 4 times with each 300 mL methanol.

Cleavage of Phycocyanobilin from Phycocyanin.

Phycocyanobilin was cleaved by boiling the Phycocyanin in 600 mL methanol under reflux with stirring for 16 hours.

Phycocyanobilin Purification.

After centrifugation at 6000 rpm 5 minutes, the volume of supernatant was reduced to around 40 mL by a rotary evaporator. Add the concentrated phycocyanobilin solution and 25 mL chloroform to 200 mL purified water with 300 µl 10.5 N HCl. Extract Phycocyanobilin to chloroform. Repeat chloroform extraction three times with 10 mL chloroform. Combine the chloroform and reduce the chloroform volume to around 10 mL by nitrogen gas. Add the chloroform solution to 60 mL hexanes. Phycocyanobilin was collected by centrifugation 3 minutes at 5000 rpm. After air dried, 112 mg phycocyanobilin obtained.

Example 3

Phycocyanobilin to Meso-Biliverdin

In 3 mL of reagent grade EtOH, 5 mg of purified phycocyanobilin was mixed with 20 mg of $NaHCO_3$ and 20 mg of $K_2CO_3$. The reaction was run for 1 day. After the reaction had run about 5 mg of crude meso-biliverdin IXα (shown below) were produced.

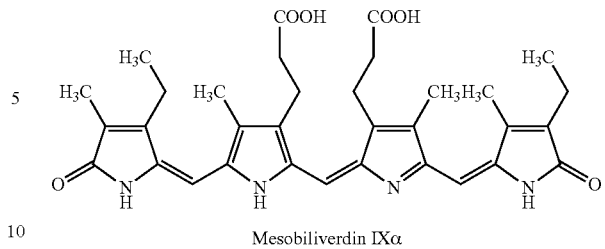

Mesobiliverdin IXα

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

What is claimed is:

1. A method of producing meso-biliverdin, the method comprising:
   reacting phycocyanobilin with an amphoteric compound to yield meso-biliverdin,
   wherein the amphoteric compound is selected from the group consisting of sodium bicarbonate, potassium carbonate, and sodium carbonate.

2. The method of claim 1, wherein the amphoteric compound is selected from the group consisting of sodium bicarbonate or potassium carbonate.

3. The method of claim 1, wherein the phycocyanobilin is reacted with the amphoteric compound in ethanol or tert-butanol.

4. The method of claim 2, wherein the phycocyanobilin is reacted with the sodium bicarbonate or the potassium carbonate in ethanol.

5. The method of claim 1, wherein the amphoteric compound is present in from 1 to 5 folds in weight compared to the phycocyanobilin by weight.

6. The method of claim 1, wherein the amphoteric compound is present in from 2 to 4 folds in weight compared to the phycocyanobilin by weight.

7. The method of claim 1, the method further comprising culturing cyanobacteria, rhodophyte, cryptophyte, or mixture thereof to yield the phycocyanobilin to be reacted with the amphoteric compound.

8. The method of claim 7, wherein the cyanobacteria, rhodophyte, cryptophyte, or mixture thereof are cultured in a culture media comprising waste water.

9. A method of producing meso-biliverdin, the method comprising:
   extracting phycocyanobilin from cyanobacteria, rhodophyte, cryptophyte, or mixture thereof; and
   isomerizing the extracted phycocyanobilin to form meso-biliverdin
   wherein isomerizing comprises reacting the extracted phycocyanobilin with an amphoteric compound selected from the group consisting of sodium bicarbonate, potassium carbonate, and sodium carbonate.

10. The method of claim 9, wherein the extracting comprises
    mixing ammonium sulfate with the cyanobacteria, rhodophyte, cryptophyte, or mixture thereof and water to yield phycocyanin,
    washing the phycocyanin with a washing solvent,
    cleaving phycocyanobilin from phycocyanin, and
    purifying the phycocyanobilin.

11. The method of claim 10, wherein the washing solvent comprises ethanol.

12. The method of claim 9, wherein the amphoteric compound is selected from the group consisting of sodium bicarbonate or potassium carbonate.

13. The method of claim 9, the method further comprising culturing cyanobacteria, rhodophyte, cryptophyte, or mixture thereof prior to extraction of phycocyanobilin.

* * * * *